(12) United States Patent
Namigata et al.

(10) Patent No.: US 12,194,161 B2
(45) Date of Patent: Jan. 14, 2025

(54) LIVING BODY-ADHESIVE SHEET (71) Applicant: Panasonic Intellectual Property Management Co., Ltd., Osaka (JP)

(72) Inventors: Yuki Namigata, Osaka (JP); Tomoko Kawashima, Osaka (JP); Takahiro Aoki, Osaka (JP); Yuko Taniike, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1006 days.

(21) Appl. No.: 17/033,679

(22) Filed: Sep. 26, 2020

(65) Prior Publication Data
US 2021/0008001 A1 Jan. 14, 2021

Related U.S. Application Data (63) Continuation of application No. PCT/JP2019/004367, filed on Feb. 7, 2019.

(30) Foreign Application Priority Data

May 17, 2018 (JP) ................. 2018-095743

(51) Int. Cl.
*A61K 9/70* (2006.01)
*A61L 27/20* (2006.01)
*C08J 5/18* (2006.01)
*C08L 1/02* (2006.01)

(52) U.S. Cl.
CPC ............ *A61K 9/7076* (2013.01); *A61L 27/20* (2013.01); *C08J 5/18* (2013.01); *C08L 1/02* (2013.01); *C08L 2203/02* (2013.01)

(58) Field of Classification Search
None
See application file for complete search history.

(56) References Cited

U.S. PATENT DOCUMENTS

| 2013/0218262 A1* | 8/2013 | Ishii ................. A61B 17/0057 623/1.36 |
| 2019/0167798 A1 | 6/2019 | Kawashima et al. |
| 2019/0328623 A1 | 10/2019 | Kusukame et al. |

FOREIGN PATENT DOCUMENTS

| CN | 109152720 A | | 1/2019 | |
| EP | 3542784 A1 | * | 9/2019 | ............. A61K 47/38 |
| JP | 2015-016612 | | 1/2015 | |
| JP | 2017164930 | * | 9/2017 | ............. A61K 47/32 |
| JP | 2017164930 A | * | 9/2017 | ............. A61K 47/32 |
| WO | 2018/092362 | | 5/2018 | |
| WO | 2018/168518 | | 9/2018 | |

OTHER PUBLICATIONS

English Translation of Chinese Search Report dated Sep. 20, 2022 for the related Chinese Patent Application No. 201980017215.5.
International Search Report of PCT application No. PCT/JP2019/004367 dated May 7, 2019.
Charles M. Hansen, "Solubility Parameters: A User's Handbook", CRC Press, Boca Raton, 2nd edn., Jun. 15, 2007, pp. 1-17, 248-249, 498-499.

* cited by examiner

*Primary Examiner* — Celeste A Roney
(74) *Attorney, Agent, or Firm* — Rimon P.C.

(57) ABSTRACT

A living body-adhesive sheet of the present disclosure includes a living body-adhesive film and a support. The living body-adhesive film has a thickness of 5 μm or less and contains cellulose. The support supports the living body-adhesive film. The support is formed of a material in which a hydrogen bonding component δH in a Hansen solubility parameter is 2 to 20 MPa$^{1/2}$.

8 Claims, 3 Drawing Sheets

LIVING BODY-ADHESIVE SHEET

BACKGROUND

1. Technical Field

The present disclosure relates to a living body-adhesive sheet.

2. Description of the Related Art

There is known a living body-adhesive sheet to be adhered to a living tissue such as skin or an organ.

For example, Japanese Unexamined Patent Application Publication No. 2015-16612 describes a nano-thin film transfer sheet. In the nano thin film transfer sheet, a first permeable substrate, a nano thin film layer, and a second permeable substrate are stacked on top of each other in this order. The first permeable substrate and the second permeable substrate are substrates that can allow a solvent to permeate or pass therethrough. The nano thin film layer is used as a skin-adhesive layer. The nano thin film layer has, for example, an A layer formed by using a solution containing a polycation, and a B layer formed by using a solution containing a polyanion. Soluble support layers and the nano thin film layer are layered between the first permeable substrate and the second permeable substrate to form a multilayer body. Subsequently, a solvent that dissolves the soluble support layers is allowed to permeate or pass through the first permeable substrate and the second permeable substrate so as to dissolve and remove the soluble support layers in the multilayer body, as a result of which a nano thin film transfer sheet is produced.

Japanese Unexamined Patent Application Publication No. 2017-164930 reports the cases in which the soluble support layers were not sufficiently removed during the production of the nano thin film transfer sheet described in Japanese Unexamined Patent Application Publication No. 2015-16612, and thus the permeable substrates could not be cleanly released from the nano thin film layer. Japanese Unexamined Patent Application Publication No. 2017-164930 describes a nano thin layer transfer sheet that addresses this issue. This nano thin layer transfer sheet has a substrate and a nano thin film layer layered on the substrate, and the substrate is a particular non-woven fabric.

SUMMARY

The techniques described in Japanese Unexamined Patent Application Publication Nos. 2015-16612 and 2017-164930 do not consider a support that can stably support a cellulose-containing, particular living body-adhesive film and that can be reliably released from the living body-adhesive film when the living body-adhesive film is being adhered to a living tissue. One non-limiting and exemplary embodiment provides a living body-adhesive sheet that is equipped with a support that can stably support a cellulose-containing particular living body-adhesive film and that can be reliably released from the living body-adhesive film when the living body-adhesive film is being adhered to a living tissue.

In one general aspect, the techniques disclosed here feature a living body-adhesive sheet including a living body-adhesive film that has a thickness of 5 μm or less and contains cellulose; and a support that supports the living body-adhesive film. The support is formed of a material in which a hydrogen bonding component δH in a Hansen solubility parameter is 2 to 20 $\text{MPa}^{1/2}$.

The support of the aforementioned living body-adhesive sheet can stably support the aforementioned cellulose-containing and living body-adhesive film and can be reliably released from the living body-adhesive film when the living body-adhesive film is being adhered to a living tissue.

Additional benefits and advantages of the disclosed embodiments will become apparent from the specification and drawings. The benefits and/or advantages maybe individually obtained by the various embodiments and features of the specification and drawings, which need not all be provided in order to obtain one or more of such benefits and/or advantages.

DETAILED DESCRIPTION

Underlying Knowledge Forming Basis of the Present Disclosure

Japanese Unexamined Patent Application Publication No. 2017-164930 suggests that a nano thin film layer having, for example, an A layer formed by using a solution containing a polycation and a B layer formed by using a solution containing a polyanion can be supported by using a particular non-woven fabric as a support. Meanwhile, the non-woven fabric described in Japanese Unexamined Patent Application Publication No. 2017-164930 does not necessarily have the properties desirable for the support for a cellulose-containing and living body-adhesive film different from the nano thin film layer described in Japanese Unexamined Patent Application Publication No. 2017-164930. The present inventors have conducted studies and found that, for example, a polypropylene non-woven fabric is not suitable as a support for a cellulose-containing and living body-adhesive film. Thus, the present inventors have further conducted studies on the material that has desirable properties as a support for a cellulose-containing and living body-adhesive film. As a result, the inventors have newly found that a material in which the hydrogen bonding component δH in the Hansen solubility parameter is in a particular range is suitable as a material for a support. The inventors have conceived of a living body-adhesive sheet of the present disclosure on the basis of this new finding.

The summary of the aspects of the present disclosure is as follows.

Item 1

A living body-adhesive sheet that includes:
a living body-adhesive film that has a thickness of 5 μm or less and contains cellulose; and
a support that supports the living body-adhesive film,
wherein the support is formed of a material in which the hydrogen bonding component (δH) in the Hansen solubility parameter (HSP) is 2 to 20 $\text{MPa}^{1/2}$.

Item 2
  The living body-adhesive sheet described in item 1, in which the support includes protrusions and recesses that are covered with the living body-adhesive film.
Item 3
  The living body-adhesive sheet described in item 2, in which the support is a non-woven fabric.
Item 4
  The living body-adhesive sheet described in any one of items 1 to 3, in which the support has a weight of 20 to 70 g/m$^2$.
Item 5
  The living body-adhesive sheet described in any one of items 1 to 4, in which the cellulose is regenerated cellulose having a weight-average molecular weight of 30,000 or more.
Item 6
  The living body-adhesive sheet described in any one of items 1 to 5, in which the living body-adhesive film is a self-supporting film having a thickness of 20 to 1300 nm.
Item 7
  The living body-adhesive sheet described in any one of items 1 to 6, in which the support is formed of at least one material selected from the group consisting of polyethylene, polyethylene terephthalate, polyacrylonitrile, polystyrene, polyvinyl chloride, polycarbonate, and polyethyleneimide.

Embodiments

The embodiments of the present disclosure will now be described with reference to the drawings. It should be noted that the embodiments described below are merely exemplary, and do not limit the living body-adhesive sheet of the present disclosure. Matters such as numerical values, shapes, materials, constituent elements, arrangement of constituent elements, connection modes, steps, and the order of steps described below in the embodiments are merely examples, and are not described with an intention to limit the present disclosure. Various embodiments described below can be combined as long as there is no conflict. Furthermore, among the constituent elements of the embodiments described below, those which are not described in an independent claim representing the broadest concept should not be interpreted as essential. In the description below, the constituent elements that have substantially identical functions may be represented by the same reference signs, and the descriptions therefor may not be repeated. Furthermore, to avoid excessive complication of the drawings, some elements may be omitted from the drawings.

Figure 1:
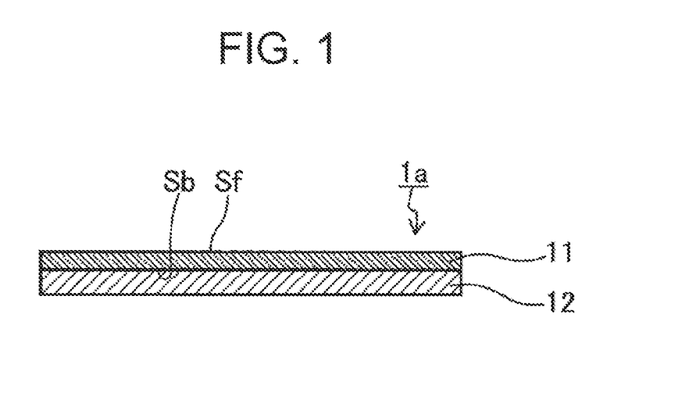
FIG. 1 is a cross-sectional view schematically illustrating one example of a living body-adhesive sheet of the present disclosure.

As illustrated in FIG. 1, a living body-adhesive sheet 1a is equipped with a living body-adhesive film 11 and a support 12 (first support). The living body-adhesive film 11 has a thickness of 5 μm or less and contains cellulose. The support 12 supports the living body-adhesive film 11. The support 12 is formed of a material in which the hydrogen bonding component δH in the Hansen solubility parameter (HSP) is 2 to 20 MPa$^{1/2}$.

The HSP is known to be a parameter that indicates the affinity between materials. The value (δ) of the HSP has a relationship represented by formula (1) below with respect to the dispersion component δD, the polar component δP, and the hydrogen bonding component δH.

$$\delta_2 = \delta D^2 + \delta P^2 + \delta H^2 \quad (1)$$

The living body-adhesive film 11 contains cellulose and contains a large quantity of hydrophilic groups. Thus, the value of the hydrogen bonding component δH, which quantitively indicates the hydrogen bonding property of the material for the support, is considered to greatly contributes to the affinity between the living body-adhesive film 11 and the support that supports the living body-adhesive film 11. The larger the value of δH of the material, the higher the affinity and the adhesion between that material and the living body-adhesive film 11. For example, δ is determined from the evaporation heat of the material, δP is determined from the dipole moment and the molecular volume, and δD is calculated from the refractive index (for example, the value measured by using sodium D lines at 25° C.) of the material. Then δH can be determined from the relationship represented by formula (1) above (see C. M. Hansen, "Hansen solubility parameters: a user's handbook", CRC Press, Boca Raton, 2nd edn., 2007).

Since δH of the material for the support 12 is 2 MPa$^{1/2}$ or more, the adhesion between the living body-adhesive film 11 and the support 12 is high, and the support 12 can stably support the living body-adhesive film 11. Meanwhile, since δH of the material for the support 12 is 20 MPa$^{1/2}$ or less, the support 12 can be reliably released from the living body-adhesive film 11 when the living body-adhesive 11 is being adhered to a living tissue. Thus, the living body-adhesive sheet 1a achieves both high adhesion of the support 12 to the living body-adhesive film 11 and a high level of the releasing property of the support 12 when the living body-adhesive film 11 is adhered to the living tissue.

The material for the support 12 may be any material that has δH of 2 to 20 MPa$^{1/2}$. The material for the support 12 may be an organic material or an inorganic material. The material for the support 12 can be, for example, a synthetic resin, a natural polymer including natural rubber or the like, or glass. The surface of the support 12 may be chemically or physically treated entirely or partially. The support 12 is, for example, formed of at least one material selected from the group consisting of polyethylene, polyethylene terephthalate, polyacrylonitrile, polystyrene, polyvinyl chloride, polycarbonate, and polyethyleneimide. The values of δH of these materials are indicated in Table 1. These values are described in C. M. Hansen, "Hansen solubility parameters: a user's handbook", CRC Press, Boca Raton, 2nd edn., 2007.

TABLE 1

| Material | Hydrogen bonding component δH of HSR [MPa$^{1/2}$] |
|---|---|
| Polyethylene | 2.8 |
| Polyethylene terephthalate | 6.6 |
| Polyacrylonitrile | 9.1 |
| Polystyrene | 2.9 |
| Polyvinyl chloride | 3.4 |
| Polycarbonate | 6.9 |
| Polyethyleneimide | 5.2-9.0 |

The shape of the living body-adhesive film 11 when the living body-adhesive film 11 is viewed in plan is not particularly limited. In a plan view, the living body-adhesive film 11 can be circular, elliptical, or polygonal. In a plan view, the living body-adhesive film 11 can have an irregular shape. The shape of the support 12 when the support 12 is viewed in plan may be the same as or different from the shape of the living body-adhesive film 11. In addition, in a plan view, the support 12 may have the same dimensions as or different dimensions from the living body-adhesive film 11. For example, more than one living body-adhesive films 11 may be disposed on one support 12. For example, when the living body-adhesive film 11 is circular in a plan view, the diameter thereof can be about 3 mm.

As illustrated in FIG. 1, the living body-adhesive film 11 has a first main surface Sb and a second main surface Sf. The support 12 is in contact with the first main surface Sb of the living body-adhesive film 11. The living body-adhesive film 11 can maintain its shape without the support 12. The support 12 can be released from the first main surface Sb of the living body-adhesive film 11. The living body-adhesive film 11 has a particular strength and can maintain its shape even after the support 12 is released.

The living body-adhesive film 11 has, for example, a tensile strength of 23 MPa or more. In such a case, for example, even when the living body-adhesive film 11 is adhered to skin, the living body-adhesive film 11 does not break easily, and the living body-adhesive film 11 can stay adhered to the skin for a long time.

The support 12 may include protrusions and recesses that are covered with the living body-adhesive film 11. As a result, in the portion where the support 12 is covered with the living body-adhesive film 11, the living body-adhesive film 11 and the support 12 are not in contact in some places, and thus the support 12 can be more easily released from the living body-adhesive film 11 when the living body-adhesive film 11 is adhered to a living tissue.

The support 12 may be, for example, a non-woven fabric, a woven fabric, an embossed substrate, a mesh material, a substrate having many pin holes, or a substrate having a rough surface formed by a blasting process or a chemical process. The support 12 is preferably a non-woven fabric.

The support 12 has, for example, a weight to 20 to 70 g/m². When the support 12 has a weight of 20 g/m² or more, the contact area between the support 12 and the living body-adhesive film 11 tends to increase. In this manner, the adhesion between the support 12 and the living body-adhesive film 11 is in a desired state, and the support 12 can more reliably and stably support the living body-adhesive film 11, Meanwhile, when the support 12 has a weight of 70 g/m² or less, an excessive increase in the contact area between the support 12 and the living body-adhesive film 11 can be avoided, and the support 12 can be more easily released from the living body-adhesive film 11 when the living body-adhesive film 11 is adhered to a living tissue. The support 12 preferably has a weight of 25 to 70 g/m² and more preferably has a weight of 25 to 65 g/m².

The support 12 has, for example, a density of 160 to 300 kg/m³.

Cellulose contained in the living body-adhesive film 11 is, for example, cellulose substantially represented by formula (I) below: Here, "cellulose substantially represented by formula (I)" means cellulose in which 90% or more of hydroxyl groups of glucose residues in cellulose represented by formula (I) remain. The ratio of the number of hydroxyl groups of glucose residues in cellulose contained in the living body-adhesive film 11 to the number of hydroxyl groups of glucose residues in cellulose represented by formula (I) can be quantitively determined by a known method, for example, X-ray photoelectron spectroscopy (XPS). Cellulose contained in the living body-adhesive film 11 may, in some cases, include a branched structure. Artificially derivatized cellulose in general does not correspond to a "cellulose substantially represented by formula (I)". Meanwhile, regenerated cellulose obtained through derivatization is not excluded from the "cellulose substantially represented by formula (I)". Cellulose regenerated through derivatization may also correspond to the "cellulose substantially represented by formula (I)".

(I)

In an embodiment of the present disclosure, the living body-adhesive film 11 is composed of regenerated cellulose. Hydrogen bonds between nanofibers constituting cellulose fibers contribute to the strength of a film formed from a suspension of natural cellulose fibers dispersed in water or the like. Thus, the only film that can be obtained is a brittle film. In contrast, in a film composed of regenerated cellulose, nanofibers are raveled to molecular chain units; thus, hydrogen bonds between cellulose molecular chains contribute to the strength of a film composed of regenerated cellulose. In other words, in a film composed of regenerated cellulose, hydrogen bonds between units smaller than nanofibers are formed evenly. Thus, compared to the case where a film is formed from a suspension of natural cellulose fibers dispersed in water or the like, there can be provided a cellulose film that has a high strength, less brittleness, and appropriate flexibility and yet withstands breaking. Here, "nanofibers" are also referred to as "nanofibrils (or microfibrils)" and are the most basic unit in which cellulose molecules aggregate. The nanofibers have a width of about 4 nm to about 100 nm and a length of, for example, about 1 μm or more.

In this description, "regenerated cellulose" refers to cellulose that does not have a crystal structure I inherent to natural cellulose. The crystal structure of cellulose can be confirmed through an XRD pattern. An XRD pattern of natural cellulose obtained by using CuK α-radiation has peaks at around 14-17° and 23° specific to the crystal structure I; however, regenerated cellulose in most cases has a crystal structure II and has peaks at around 12°, 20°, and 22° but not around 14-17° and 23°.

For example, regenerated cellulose not chemically modified or derivatized accounts for 90% or more of regenerated cellulose contained in the living body-adhesive film 11 on a mass basis. Preferably, regenerated cellulose not chemically modified or derivatized can account for 98% or more of regenerated cellulose contained in the living body-adhesive film 11 on a mass basis. In this case, a large quantity of cellulose not chemically modified or derivatized is contained in the living body-adhesive film 11, and thus it is considered that more hydroxyl groups are contained per cellulose molecular chain. Thus, it is considered that more hydrogen bonds are formed between cellulose molecules, and the living body-adhesive film 11 tends to exhibit high strength. Regenerated cellulose contained in the living body-adhesive film 11 may be un-crosslinked.

The material for regenerated cellulose is not particularly limited. Examples of the material for regenerated cellulose include plant-origin natural cellulose, biological natural cellulose, regenerated cellulose such as cellophane, and processed cellulose such as cellulose nanofibers. The impurity concentration in the material for regenerated cellulose is advantageously 10 wt % or less.

Furthermore, since cellulose exhibits amphiphilicity, hydrophilic active ingredients and hydrophobic active ingredients can be appropriately carried, and thus the living body-adhesive film 11 has high versatility.

The living body-adhesive film 11 has, for example, a thickness of 20 to 5000 nm. As long as the thickness of the living body-adhesive film 11 is 20 nm or more, the living body-adhesive film 11 has high strength and is easy to handle. Thus, the living body-adhesive film 11 can function as a self-supporting film that can be adhered to a living tissue. As long as the thickness of the living body-adhesive film 11 is 5000 nm or less, the living body-adhesive film 11 can be easily adhered when the living body-adhesive film 11 is being adhered to a living tissue. When the thickness of the living body-adhesive film 11 is within this range, for example, the living body-adhesive film 11 can be easily released from a living tissue by using running water. The thickness of the living body-adhesive film 11 is determined by, for example, measuring the thickness of the living body-adhesive film 11 at more than one positions and averaging the results. The thickness at each position can be measured by using, for example, a stylus profiling system DEKTAK (registered trademark) produced by Bruker Nano incorporated.

The thickness of the living body-adhesive film 11 may be 100 nm or more. When the thickness of the living body-adhesive film 11 is 100 nm or more, the living body-adhesive film 11 has high strength and is easy to handle. The thickness of the living body-adhesive film 11 may be 300 nm or more. When the thickness of the living body-adhesive film 11 is 300 nm or more, the living body-adhesive film 11 has higher strength, withstands breaking, and is easy to use. The thickness of the living body-adhesive film 11 may be 500 nm or more. When the thickness of the living body-adhesive film 11 is 500 nm or more, more active ingredients, such as beauty ingredients, can be retained in the living body-adhesive film 11. The thickness of the living body-adhesive film 11 may be 2000 nm or less. When the thickness of the living body-adhesive film 11 is 2000 nm or less, the living body-adhesive film 11 closely adheres to a living tissue, and the living body-adhesive film 11 can be stably adhered to a surface of a living tissue, such as skin. The thickness of the living body-adhesive film 11 may be 1300 nm or less. When the thickness of the living body-adhesive film 11 is 1300 nm or less, the living body-adhesive film 11 more closely adheres to a living tissue, and the state in which the living body-adhesive film 11 is stably adhered to a surface of a living tissue, such as skin, can be maintained for a long time.

Regenerated cellulose contained in the living body-adhesive film 11 has, for example, a weight-average molecular weight of 30,000 or more. In this case, the thickness of the living body-adhesive film 11 can be easily adjusted to 5 μm or less.

Cellulose contained in the living body-adhesive film 11 can be regenerated cellulose having a weight-average molecular weight of 150,000 or more. In this case, the living body-adhesive film 11 can be prepared as a self-supporting film having a thickness of 20 to 1300 nm. Since cellulose contained in the living body-adhesive film 11 has a high molecular weight, the strength along the direction in which cellulose molecular chains extend in the living body-adhesive film 11 is high, and, in addition, more hydroxyl groups are contained in one molecular chain. It is considered that, as a result of this, a large number of intermolecular hydrogen bonds can be formed, and a thin but strong film can be formed. In this description, a "self-supporting film" refers to a film that can maintain its film shape without any support. For example, when a part of a self-supporting film is pinched and lifted with fingers or tweezers, the entire self-supporting film can be lifted without any support and without damaging the self-supporting film.

One possible material for a skin-adhesive film is polylactic acid. However, since polylactic acid is a hydrophobic material, a portion of a living body to which the film adheres can become damp, and thus a polylactic acid film is not necessarily suitable for a long-time use. In contrast, cellulose has biocompatibility, and rarely inflicts physical or chemical stress to skin even when cellulose is directly adhered to the skin. In addition, since cellulose is amphiphilic and does not dissolve in water while exhibiting hydrophilicity, the living body-adhesive film 11 does not dissolve in moisture such as sweat, and thus offers excellent durability.

The living body-adhesive film 11 is, for example, used by being adhered to skin in a region such as a face or an arm. Thus, the living body-adhesive film 11 typically has an area of 7 $mm^2$ or more. In this manner, a wide region can be covered when the living body-adhesive film 11 is adhered to skin. Alternatively, the living body-adhesive film 11 may be adhered to a surface of a living tissue, such as an organ, other than skin. The living body-adhesive film 11 adhering to the surface of an organ can protect the organ. For example, adhesion between organs can be prevented.

Cellulose contained in the living body-adhesive film 11 has, for example, a crystallinity of 0 to 12%. In this case, the quantity of hydroxyl groups involved in crystal structure formation is appropriately small, and thus adhesion of the living body-adhesive film 11 to a living body tends to be high. It should noted that the living body-adhesive film 11 can exhibit various functions by specifically chemically modifying sites where hydroxyl groups are supposed to be present.

The living body-adhesive film 11 has, for example, a bulk density of 0.3 to 1.5 $g/cm^3$. When the bulk density of the living body-adhesive film 11 is 0.3 $g/cm^3$ or more, the living body-adhesive film 11 tends to have strength necessary to maintain the shape of the living body-adhesive film 11. When the living body-adhesive film 11 is to be adhered to a living body, a liquid or cream fitting agent such as water or cosmetic lotion is sometimes applied between the living body-adhesive film 11 and the living body. Alternatively, the living body-adhesive film 11 in some cases retains active ingredients, such as a cosmetic, a beauty ingredient, and a medicinal ingredient, that act on the living body or protect the living body. For example, these ingredients can be retained in the voids of the living body-adhesive film 11. When the living body-adhesive film 11 has a bulk density of 1.5 $g/cm^3$ or less, active ingredients can easily permeate into the living body-adhesive film 11. In the living body-adhesive film 11, active ingredients that act on a living body or that protect a living body and that exist in voids of the living body-adhesive film 11 can be in a solid, solution, dispersion, or emulsion state. The true density of cellulose is about 1.5 $g/cm^3$.

As mentioned above, the living body-adhesive film 11 can retain active ingredients that act on the living body or protect the living body. In such a case, the active ingredients may exist inside the living body-adhesive film 11 or on a surface of the living body-adhesive film 11. Whether or not the living body-adhesive film 11 retains active ingredients can be confirmed by, for example, infrared spectroscopy. Since the living body-adhesive film 11 contains cellulose, which has hydrophilicity, the living body-adhesive film 11 can retain water-soluble ingredients. Meanwhile, since cellulose is amphiphilic and has both hydrophilicity and hydrophobicity, hydrophobic ingredients can also be retained in the living body-adhesive film 11. Examples of the water-soluble ingredients that can be retained in the living body-adhesive film 11 include hyaluronic acid, vitamin B, vitamin C, vitamin C derivatives, collagen, and placenta. Examples of the hydrophobic ingredients that can be retained in the living body-adhesive film 11 include vitamin A, vitamin E, ceramide, and fullerenes. The active ingredients retained in the living body-adhesive film 11 can be medicinal ingredients. Examples of the medicinal ingredients include tacrolimus, isosorbide dinitrate, finasteride, and minoxidil. The active ingredients retained in the living body-adhesive film 11 can be sunscreen agents. A sunscreen agent contains, for example, an ultraviolet ray-absorbing material, such as dioxybenzone and 2-ethylhexyl 4-methoxycinnamate, or an ultraviolet ray-scattering material, such as titanium oxide or zinc oxide.

The living body-adhesive film 11 may be a single-layer film or a film having a multilayer structure including multiple layers. When the living body-adhesive film 11 is a film having a multilayer structure, the active ingredients retained in the layers may be the same or may be different from one layer to the other. The living body-adhesive film 11 may have a multilayer structure in which a cellulose-containing layer and a layer formed of a material other than cellulose are stacked.

At least part of the living body-adhesive film 11 may be colored. For example, at least part of the living body-adhesive film 11 may have a color close to the color of skin. In such a case, spots, moles, and scars on the skin can be covered with the living body-adhesive film 11 and made inconspicuous. Note that a living body-adhesive film 11 adhered to the skin to cover a scar can protect the scar from external stimuli. In such a case, the living body-adhesive film 11 may retain a medicinal ingredient for treating the scar. Moreover, a living body-adhesive film 11 may have a particular design or color provided by printing. In such a case, for example, the living body-adhesive film 11 can be used as a decorative sheet such as a tattoo sticker.

The living body-adhesive film 11 has, for example, a water vapor transmission rate (WVTR) of $1 \times 10^4$ g/m$^2$·24 h or more. In this manner, the living body-adhesive film 11 allows moisture such as sweat to pass smoothly, a portion of a living body to which the living body-adhesive film 11 is adhered rarely becomes damp, and thus discomfort caused by dampness can be reduced.

The living body-adhesive film 11 has, for example, a contact angle of 0° to 30° with respect to water. When the living body-adhesive film 11 has a contact angle within this range with respect to water, the affinity between the surface of the living body-adhesive film 11 and moisture is increased, and, for example, the moisture on skin can be rapidly absorbed by the living body-adhesive film 11. As a result, the living body-adhesive film 11 adhered to skin has high stability and offers high comfort.

Figure 2A:
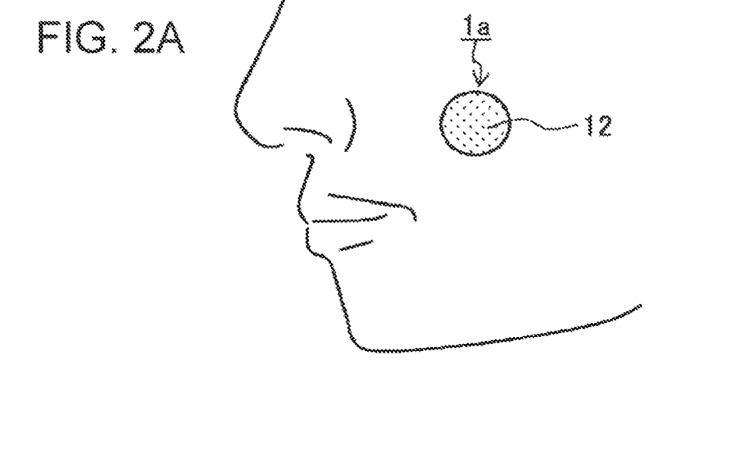
FIG. 2A is a diagram illustrating how the living body-adhesive sheet of the present disclosure is used.

One example of a method for using the living body-adhesive sheet 1a will now be described. The living body-adhesive film 11 in the living body-adhesive sheet 1a is, for example, adhered to face skin. Alternatively, the living body-adhesive film 11 may be adhered to arm skin or a living tissue other than skin. As illustrated in FIG. 2A, for example, the living body-adhesive sheet 1a is brought close to a particular site (for example, skin) of a living body while arranging the second main surface Sf of the living body-adhesive film 11 to face this site. Here, a liquid or cream fitting agent may be applied to the particular site of the living body or the second main surface Sf of the living body-adhesive film 11. This fitting agent contains, for example, water, oil or fat, an alcohol, or an emulsifier, and may further contain at least one active ingredient selected from those described above.

Figure 2B:
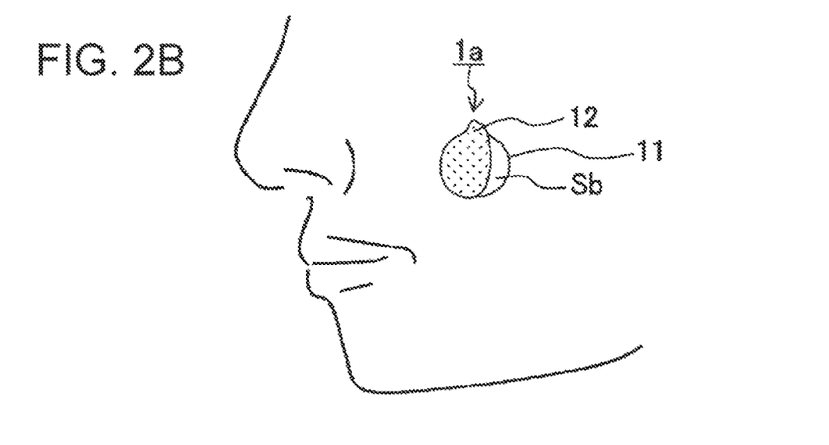
FIG. 2B is a diagram illustrating how the living body-adhesive sheet of the present disclosure is used.
Figure 2C:
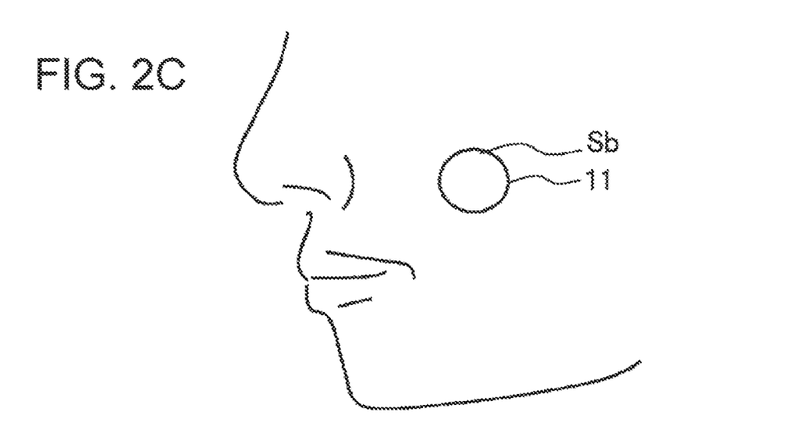
FIG. 2C is a diagram illustrating how the living body-adhesive sheet of the present disclosure is used.

Next, the second main surface Sf of the living body-adhesive film 11 is allowed to contact the particular site of the living body, and the living body-adhesive sheet 1a is adhered to the particular site of the living body. Subsequently, as illustrated in FIG. 2B, the support 12 is released from the first main surface Sb of the living body-adhesive film 11. Here, the living body-adhesive film 11 stays adhered to the living body. When the support 12 is completely released, as illustrated in FIG. 2C, the entire first main surface Sb of the living body-adhesive film 11 becomes exposed.

One example of a method for producing the living body-adhesive sheet 1a is described. First, cellulose is dissolved in a solvent to prepare a cellulose solution. From the viewpoint of forming a living body-adhesive film 11 having a thickness of 5 μm or less, for example, a cellulose solution is prepared by using cellulose having a weight-average molecular weight of 30,000 or more. If needed, a cellulose solution is prepared by using cellulose having a weight-average molecular weight of 150,000 or more so that the living body-adhesive film 11 contains regenerated cellulose that has a weight-average molecular weight of 150,000 or more. In this case, a self-supporting living body-adhesive film 11 having a thickness of 1300 nm or less can be prepared, Cellulose used to prepare the cellulose solution may be any cellulose having the desired weight-average molecular weight. Cellulose used in preparing the cellulose solution can be, for example, plant-origin cellulose such as pulp or cotton, or cellulose generated by a living organism such as bacteria. The impurity concentration in the material for cellulose is, for example, 10 wt % or less.

When the weight-average molecular weight of regenerated cellulose is 2,000,000 or less, handling ease is advantageously improved. More desirably, the weight-average molecular weight of regenerated cellulose is 1,000,000 or less.

The solvent is a solvent (first solvent) that contains at least an ionic liquid, for example. By using the first solvent, cellulose having a weight-average molecular weight of 150,000 or more can be dissolved in a relatively short time. The ionic liquid is a salt constituted by an anion and a cation, and can exhibit a liquid state at a temperature of 150° C. or less. The ionic liquid contained in the first solvent contains, for example, an amino acid or an alkyl phosphoric acid ester. Since the first solvent contains such an ionic liquid, cellulose can be dissolved while suppressing the decrease in the molecular weight of cellulose. In particular, since the amino acid is a component present in a living body, an ionic liquid that contains an amino acid is advantageous in forming a living body-adhesive film 11 that is more safe for the living body.

Cellulose may be dissolved by using an ionic liquid that has been diluted in advance with a solvent that does not cause precipitation of cellulose. For example, a mixture of an aprotic polar solvent and an ionic liquid may be used as the first solvent. An aprotic polar solvent rarely forms hydrogen bonds and rarely allows precipitation of cellulose.

The ionic liquid contained in the first solvent is, for example, an ionic liquid represented by formula (II) below. The anion in the ionic liquid represented by formula (II) is an amino acid. As described in formula (II), the anion in this ionic liquid contains a terminal carboxyl group and a terminal amino group. The cation in the ionic liquid represented by formula (II) may be a quaternary ammonium cation.

(II)

In formula (II), $R_1$ to $R_6$ each independently represent a hydrogen atom or a substituent. The substituent can be an alkyl group, a hydroxyalkyl group, or a phenyl group. The substituent may contain branches in the carbon chain. The substituent may contain a functional group such as an amino group, a hydroxyl group, or a carboxyl group.

The ionic liquid contained in the first solvent may be an ionic liquid represented by formula (III) below. In formula (III), $R_1$, $R_2$, $R_3$, and $R_4$ each independently represent a hydrogen atom or an alkyl group having 1 to 4 carbon atoms.

(III)

A second solvent may be further added in the step of preparing the cellulose solution. For example, the second solvent may be further added to a mixture of the first solvent and cellulose having a particular weight-average molecular weight. The second solvent is, for example, a solvent that does not allow precipitation of cellulose. The second solvent can be, for example, an aprotic polar solvent.

The cellulose concentration in the cellulose solution is typically 0.2 to 15 wt %. As long as the cellulose concentration in the cellulose solution is 0.2 wt % or more, a living body-adhesive film 11 that has a strength necessary to keep its shape can be obtained while decreasing the thickness of the living body-adhesive film 11. As long as the cellulose concentration in the cellulose solution is 15 wt % or less, precipitation of cellulose in the cellulose solution can be suppressed. The cellulose concentration in the cellulose solution may be 1 to 10 wt %. When the cellulose concentration in the cellulose solution is 1 wt % or more, a living body-adhesive film 11 that has a higher strength is obtained. When the cellulose concentration in the cellulose solution is 10 wt % or less, a stable cellulose solution with less precipitation of cellulose can be prepared.

Next, the cellulose solution is applied to a surface of a substrate to form a liquid film on the surface of the substrate. The contact angle of the surface of the substrate with respect to water is, for example, 90° or less. In this case, the wettability of the cellulose solution to the substrate is appropriate, and a liquid film that spreads along the surface of the substrate can be stably formed. The material for the substrate is not particularly limited. The substrate typically has a nonporous structure having a flat and smooth surface. In this case, penetration of the cellulose solution into the inside of the substrate can be prevented, and the living body-adhesive film 11 can be easily released from the substrate in the later step.

The substrate may be chemically or physically surface-modified. A polymer material substrate subjected to a surface modification treatment such as ultraviolet (UV) irradiation or corona treatment may be used as the substrate, for example. For example, application of a surface modifying agent, surface modification, plasma treatment, sputtering, etching, or blasting can be applied as the surface modification method.

Examples of the method for forming a liquid film of a cellulose solution on a substrate include a gap coating method that involves forming a particular gap between the surface of the substrate and an applicator or the like, a slot die coating method, a spin coating method, a metering rod coating method that uses a bar coater, and a gravure coating method. The thickness of the living body-adhesive film 11 can be adjusted by adjusting the concentration of the cellulose solution and the thickness of a liquid film adjusted by the coating speed and the gap thickness or the size of the slot die opening, the rotation speed of spin coating, the groove depth or coating speed of a bar coater or a gravure coating, or the like. The method for forming a liquid film of the cellulose solution on a substrate may be a casting method, screen printing that uses a squeegee, spray coating, or electrostatic atomization.

When the liquid film of the cellulose solution is being formed on the substrate, at least one of the cellulose solution and the substrate may be heated. This heating may be performed in a temperature range (for example, 40° C. to 100° C.) in which the cellulose solution can stay stable.

The liquid film of the cellulose solution formed on the substrate may be heated. Heating of the liquid film is performed at, for example, a temperature (for example, 50° C. to 200° C.) lower than the decomposition temperature of the ionic liquid contained in the first solvent. Heating of the liquid film may be performed at a temperature lower than the decomposition temperature of the ionic liquid and lower than the boiling point of the second solvent. When the liquid film is heated at such a temperature, solvents (for example, the second solvent and the like) other than the ionic liquid can be appropriately removed, and the strength of the living body-adhesive film 11 tends to be high. In addition, quality degradation in the living body-adhesive film 11 caused by bumping of the solvents in the cellulose solution can be suppressed. The liquid film may be heated in a reduced pressure environment. In such a case, the solvents other than the ionic liquid can be appropriately removed in a shorter period of time at a temperature lower than the boiling points of the solvents.

After the liquid film of the cellulose solution is formed on the substrate, the liquid film may be gelated. For example, the liquid film is exposed to vapor of a liquid that can be dissolved in the ionic liquid but that does not dissolve cellulose so as to gelate the liquid film, and a polymer gel sheet can be obtained as a result. For example, when the liquid film is left to stand in an environment having a relative humidity of 30% to 100% RH, the ionic liquid in the liquid film comes into contact with water, and the solubility of cellulose in the liquid film decreases. As a result, some of cellulose molecules precipitate and form a three-dimensional structure. As a result, the liquid film is gelated. The absence or presence of the gel point can be determined by whether the gelated film can be lifted up or not.

Heating of the liquid film may be performed before, after, or before and after gelation of the liquid film.

Next, the substrate and the polymer gel sheet are immersed in a rinsing solution, which is a liquid that does not dissolve cellulose. In this step, the ionic liquid is removed from the polymer gel sheet. This step can be understood as a step of washing the polymer gel sheet. In this step, in addition to the ionic liquid, some of the components in the cellulose solution other than cellulose and the ionic liquid may be removed (for example, the second solvent may be removed). The rinsing solution is typically a liquid that can be dissolved in the ionic liquid. Examples of such a solution include water, methanol, ethanol, propanol, butanol, octanol, toluene, xylene, acetone, acetonitrile, dimethylacetamide, dimethylformamide, and dimethylsulfoxide.

Next, components such as solvents are removed from the polymer gel sheet. In other words, the polymer gel sheet is dried. When the polymer gel sheet is dried while being placed on a substrate such as a non-woven fabric during this process, the dried polymer gel sheet can be easily separated from the substrate. A drying method such as natural drying, vacuum drying, heat drying, freeze drying, or supercritical drying can be applied as the method for drying the polymer gel sheet. The method for drying the polymer gel sheet may be vacuum heating. The conditions for drying the polymer gel sheet are not particularly limited. As the conditions for drying the polymer gel sheet, the time and temperature sufficient to remove the second solvent and the rinsing solution are selected. The living body-adhesive film 11 is obtained by removing the solvents from the polymer gel sheet.

In the step of drying the polymer gel sheet, the bulk density of the living body-adhesive film 11 can be adjusted to a relatively high level by applying natural drying, vacuum drying, or heat drying, and thus a robust living body-adhesive film 11 can be obtained. When freeze drying or supercritical drying is applied in the step of drying the polymer gel sheet, a living body-adhesive film 11 that has a low bulk density is easily obtained compared to the case in which natural drying, vacuum drying, or heat drying is applied. The bulk density of the living body-adhesive film 11 may be adjusted by adjusting the cellulose concentration in the liquid film and the types of solvents staying in the polymer gel sheet during drying of the polymer gel sheet. When the bulk density of the living body-adhesive film 11 is low, the living body-adhesive film 11 can retain larger quantities of active ingredients such as liquid ingredients and/or beauty ingredients.

When freeze drying is applied in the step of drying the polymer gel sheet, for example, a solvent that can be frozen and has a boiling point near 100° C. to 200° C. is used. For example, freeze drying can be performed by using a solvent such as water, tert-butyl alcohol, acetic acid, 1,1,2,2,3,3,4-heptafluorocyclopenane, or dimethylsufoxide. It is advantageous if the solvent used for freeze drying is a solvent that can be dissolved in the rinsing solution. However, freeze drying can be applied even when the solvent used in freeze drying is a solvent that does not dissolve in the rinsing solution. For example, after the polymer gel sheet is immersed in the rinsing solution, the rinsing solution remaining in the polymer gel sheet is replaced by a solvent that can be dissolved in the rinsing solution. Furthermore, this solvent is replaced by a solvent for freeze drying so that freeze drying can be applied in drying the polymer gel sheet.

In order to allow retention of the active ingredients such as beauty ingredients, the polymer gel sheet can be immersed in the solution of the active ingredients before and/or after the step of drying the polymer gel sheet. Here, the solution may contain more than one active ingredients. The solvent in the solution is at least one solvent selected from the group consisting of water, methanol, ethanol, propanol, butanol, octanol, toluene, xylene, acetone, acetonitrile, dimethylacetamide, dimethylformamide, and dimethylsulfoxide. Instead of immersing the polymer gel sheet in the solution, a tacky component may be applied to the polymer gel sheet by atomization, vapor deposition, or coating. The polymer gel sheet may be immersed in a solution, dispersion, or emulsion containing the aforementioned active ingredients in addition to the immersion in a solution of the tacky component.

As a result, a living body-adhesive film 11 is obtained. Subsequently, for example, a living body-adhesive sheet 1a is obtained by separating the living body-adhesive film 11 from the substrate and placing the living body-adhesive film 11 on the support 12. In the step of drying the polymer gel sheet, the support 12 can be used as the substrate on which the polymer gel sheet is placed. In this case, there is no need to separate the living body-adhesive film 11 from the substrate in order to produce a living body-adhesive sheet 1a.

The living body-adhesive sheet 1a can be altered from various viewpoints. For example, the living body-adhesive sheet 1a may be altered to a living body-adhesive sheet 1b illustrated in FIG. 3. The living body-adhesive sheet 1b has features identical to those of the living body-adhesive sheet 1a except for those that are described particularly. The constituent elements of the living body-adhesive sheet 1b identical or corresponding to the constituent elements of the living body-adhesive sheet 1a are denoted by the same reference signs, and the detailed descriptions therefor are not repeated. The descriptions regarding the living body-adhesive sheet 1a also hold true for the living body-adhesive sheet 1b unless technically inconsistent.

Figure 3:
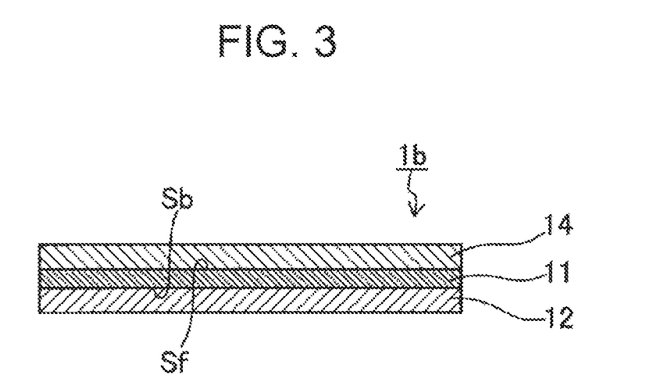
FIG. 3 is a cross-sectional schematically illustrating another example of the living body-adhesive sheet of the present disclosure.

As illustrated in FIG. 3, the living body-adhesive sheet 1b is further equipped with a support 14 (second support). The support 14 is in contact with the second main surface Sf of the living body-adhesive film 11. The support 14 is formed of the same material as or a different material from the material for the support 12. The support 14 may have the same size as or a different size from the living body-adhesive film 11 in a plan view. The support 14 may have the same size as or a different size from the support 12 in a plan view. Typically, the support 14 can be released from the living body-adhesive film 11. The support 14 can protect the living body-adhesive film 11 before the living body-adhesive sheet 1b is used, and facilitates handling of the living body-adhesive sheet 1b when the living body-adhesive sheet 1b is used.

When the living body-adhesive sheet 1b is used, first, the support 14 is released from the living body-adhesive film 11. As a result, the second main surface Sf becomes exposed. Subsequently, the second main surface Sf is brought close to a particular site of the living body, and the living body-adhesive film 11 is adhered to the particular site of the living body in the same manner as the living body-adhesive sheet 1a.

EXAMPLES

The living body-adhesive sheet of the present disclosure will now be described in further detail through examples. It should be noted that the living body-adhesive sheet of the present disclosure is not limited by the examples below.

Example 1

Cellulose having a purity of 90% or higher and derived from bleached pulp made from wood was prepared. Cellulose derived from bleached pulp was dissolved in an ionic liquid to prepare a cellulose solution. An ionic liquid represented by formula (III) above with $R_1$ representing a methyl group and each of $R_2$, $R_3$, and $R_4$ representing an ethyl group was used as the ionic liquid.

Next, a substrate having a flat surface was prepared. The cellulose solution was applied to a surface of the substrate by gap coating to form a liquid film of the cellulose solution on the substrate. Here, the size of the gap was adjusted so that the thickness of the living body-adhesive film containing regenerated cellulose was to be 200 nm. After forming the liquid film of the cellulose solution, the substrate and the liquid film were left standing in a 20° C., 40% to 60% RH environment for a sufficient period of time to gelate the liquid film. As a result, a polymer gel sheet was obtained. Subsequently, the polymer gel sheet was immersed in water and washed with water to remove the ionic liquid from the polymer gel sheet. Next, a multilayer body of the washed substrate and polymer gel sheet was stacked on a polyethylene non-woven fabric having δH of 2.8 $MPa^{1/2}$ by bringing the polymer gel sheet and the non-woven fabric to contact each other. Next, the non-woven fabric and the polymer gel sheet were heat-dried, and a living body-adhesive sheet of Example 1 was obtained as a result. In the living body-adhesive sheet of Example 1, the living body-adhesive film derived from the polymer gel sheet was supported on the non-woven fabric. The living body-adhesive film had a transparent appearance.

The thickness of the living body-adhesive film was measured at more than one positions, and the measured values were averaged to determine the thickness d of the living body-adhesive film. The thickness d of the living body-adhesive film of the living body-adhesive sheet of Example 1 was about 210 nm. The bulk density dB of the living body-adhesive film was 1.5 $g/cm^3$. The bulk density dB was determined from formula (2) below. In formula (2), W represents the mass of a test piece cut out from the living body-adhesive film, d represents the thickness of the test piece, and $A_p$ represents the area of the test piece.

$$dB = W/(A_p d) \quad (2)$$

The crystallinity of the living body-adhesive film of the living body-adhesive sheet of Example 1 was determined in accordance with the method that uses $^{13}$C-NMR reported in Park et al. "Cellulose crystallinity index: measurement techniques and their impact on interpreting cellulase performance", Biotechnology for Biofuels 2010, 3:10. According to this method, in a spectrum obtained by solid-state $^{13}$C-NMR measurement, the peak at around 87 to 93 ppm is treated as a peak derived from a crystal structure, and a broad peak at around 80 to 87 ppm is treated as a peak derived from a non-crystal structure. When the peak area of the former is represented by X and the latter by Y, the crystallinity is determined from formula (3) below. In formula (3), "×" indicates multiplication.

$$\text{Crystallinity [\%]} = (X/(X+Y)) \times 100 \quad (3)$$

In $^{13}$C-NMR measurement, Unity Inova-400 produced by Varian and a 5 mm CP/MAS probe produced by Doty Scientific, Inc., were used, and the CP/MAS method was applied. The measurement conditions were as follows: MAS rate: 10 kHz, room temperature (25° C.), sample rotation rate: 10 kHz, observation width: 30.2 kHz, observation center: 96 ppm, observation frequency: 100.574 MHz. A CP pulse ($^1H \rightarrow {}^{13}C$) method was conducted under observation nucleus 90° pulse: 3.9 μsec, 1H excitation pulse: 3.8 μsec, contact time: 2.0 msec, waiting time: 10 sec or more, number of scans: 8,000. The solid phase $^{13}$C-NMR spectrum of cellulose measured by the CP method under the aforementioned conditions was confirmed to show good match with a solid-phase $^{13}$C-NMR spectrum measured by a dipolar decouple (DD) method by setting a sufficient relaxation time. Here, the reference substance for solid phase $^{13}$C-NMR was tetramethylsilane (TMS). The determined crystallinity of the living body-adhesive film of the living body-adhesive sheet of Example 1 was 0%.

The weight-average molecular weight of the living body-adhesive film of the living body-adhesive sheet of Example 1 measured by a gel permeation chromatography (GPC)-multi angle light scattering (MALS) method was about 224,000. In this measurement, a liquid feeder LC-20AD produced by Shimadzu Corporation and, as detectors, a differential refractometer Optilab rEX and a multi-angle light scattering detector DAWN HELEOS produced by Wyatt Technology Corporation were used. As the column, TSKgel α-M produced by Tosoh Corporation was used, and dimethyl acetamide doped with 0.1 M of lithium chloride was used as the solvent. The measurement was performed under conditions of: column temperature: 23° C., flow rate: 0.8 mL/min.

Example 2

A living body-adhesive sheet of Example 2 was prepared as in Example 1 except that a polyethylene terephthalate non-woven fabric having δH of 6.6 $MPa^{1/2}$ was used instead of the polyethylene non-woven fabric.

Example 3

A living body-adhesive sheet of Example 3 was prepared as in Example 1 except that a polyacrylonitrile non-woven fabric having δH of 9.1 $MPa^{1/2}$ was used instead of the polyethylene non-woven fabric.

Comparative Example 1

A living body-adhesive sheet of Comparative Example 1 was prepared as in Example 1 except that a polypropylene non-woven fabric having δH of 1.0 $MPa^{1/2}$ was used instead of the polyethylene non-woven fabric. However, the living body-adhesive film derived from the polymer gel sheet did not at all adhere to the non-woven fabric but stay detached. Thus, it was difficult to install the film with good adhesion.

Comparative Example 2

A living body-adhesive sheet of Comparative Example 2 was prepared as in Example 1 except that a nylon 66 non-woven fabric having δH of 24.0 $MPa^{1/2}$ was used instead of the polyethylene non-woven fabric.

Comparative Example 3

A living body-adhesive sheet of Comparative Example 3 was prepared as in Example 1 except that a cellulose non-woven fabric having δH of 29.7 $MPa^{1/2}$ was used instead of the polyethylene non-woven fabric.

Comparative Example 4

Polylactic acid having a weight-average molecular weight of 250,000 was dissolved in chloroform to prepare a 1.5 wt % polylactic acid solution. The polylactic acid solution was applied by spin coating (rotation rate: 2000 rpm) to a substrate having a polyvinyl alcohol film having a weight-average molecular weight of about 500 formed thereon in advance, and then chloroform, that is, the solvent, was evaporated. Next, polyvinyl alcohol was removed by immersion in water, and the resulting polylactic acid film was placed on a polyethylene terephthalate non-woven fabric. However, the polylactic acid film did not at all adhere to the non-woven fabric but stay detached. Thus, it was difficult to install the film with good adhesion.

Evaluation of Installation State

The adhered state between the non-woven fabric and the living body-adhesive film in each of the living body-adhesive sheets of Examples and Comparative Examples was visually checked, and the installation state of the living body-adhesive film with respect to the non-woven fabric was evaluated on the basis of the following evaluation standard. The results are shown in Table 2.

AA: The area of a region where the living body-adhesive film is detached from the non-woven fabric is less than 10% of the total area of the living body-adhesive film.

A: The area of a region where the living body-adhesive film is detached from the non-woven fabric is 10% or more but less than 50% of the total area of the living body-adhesive film.

C: The area of a region where the living body-adhesive film is detached from the non-woven fabric is 50% or more of the total area of the living body-adhesive film.

Evaluation of Skin-Adhesive Property

The skin-adhesive property of the living body-adhesive sheets of Examples 1 to 3 and Comparative Examples 2 and 3 was evaluated by the following method. Onto skin, 20 μL of an aqueous glycerin solution (glycerin concentration: 30 wt %) was dropped. Then a 1.5 cm-square living body-adhesive film of each of the living body-adhesive sheets of Examples 1 to 3 and Comparative Examples 2 and 3 was adhered to an anterior forearm region, and the non-woven fabric was removed. Here, the case where the living body-adhesive film was released from the non-woven fabric and adhered to the skin was evaluated as pass, and the case where the living body-adhesive film did not adhered to the skin was evaluated as fail. The results are shown in Table 2.

Table 2 shows that when $\delta H$ of the non-woven fabric is 2 $MPa^{1/2}$ or more, the adhesion between the living body-adhesive film and the non-woven fabric increases, and thus the living body-adhesive film can be stably installed onto the non-woven fabric. In contrast, when $\delta H$ of the non-woven fabric is 20 $MPa^{1/2}$ or more, the adhesion between the living body-adhesive film and the non-woven fabric increases excessively, and thus it becomes difficult to adhere the living body-adhesive film to the skin. Thus, it was found that, as long as $\delta H$ of the non-woven fabric is 2 to 20 $MPa^{1/2}$, the living body-adhesive film and the support adhere to each other appropriately, and both stable support of the living body-adhesive film and ease of adhering the living body-adhesive film to skin can be achieved.

Example 4

A living body-adhesive sheet of Example 4 was prepared as in Example 1 except that a polyethylene terephthalate non-woven fabric having a weight of 20 $g/m^2$ was used instead of the polyethylene non-woven fabric.

Example 5

A living body-adhesive sheet of Example 5 was prepared as in Example 1 except that a polyethylene terephthalate non-woven fabric having a weight of 30 $g/m^2$ was used instead of the polyethylene non-woven fabric.

Example 6

A living body-adhesive sheet of Example 6 was prepared as in Example 1 except that a polyethylene terephthalate non-woven fabric having a weight of 40 $g/m^2$ was used instead of the polyethylene non-woven fabric.

Example 7

A living body-adhesive sheet of Example 7 was prepared as in Example 1 except that a polyethylene terephthalate non-woven fabric having a weight of 50 $g/m^2$ was used instead of the polyethylene non-woven fabric.

Example 8

A living body-adhesive sheet of Example 8 was prepared as in Example 1 except that a polyethylene terephthalate

TABLE 2

| | Material for living body-adhesive film | Material for support | $\delta H$ of support ($MPa^{1/2}$) | Installation state | Skin-adhesive property |
|---|---|---|---|---|---|
| Example 1 | Cellulose | Polyethylene | 2.8 | AA | Pass |
| Example 2 | Cellulose | Polyethylene terephthalate | 6.6 | AA | Pass |
| Example 3 | Cellulose | Polyacrylonitrile | 9.1 | AA | Pass |
| Comparative Example 1 | Cellulose | Polypropylene | 1.0 | C | — |
| Comparative Example 2 | Cellulose | Nylon 66 | 24.0 | AA | Fail |
| Comparative Example 3 | Cellulose | Cellulose | 29.7 | AA | Fail |
| Comparative Example 4 | Polylactic acid | Polyethylene terephthalate | 6.6 | C | — | non-woven fabric having a weight of 60 g/m² was used instead of the polyethylene non-woven fabric.

Example 9

A living body-adhesive sheet of Example 9 was prepared as in Example 1 except that a polyethylene terephthalate non-woven fabric having a weight of 70 g/m² was used instead of the polyethylene non-woven fabric.

Evaluation of Installation State

The installation state of the living body-adhesive film with respect to the non-woven fabric was evaluated as in Examples 1 to 3 and Comparative Examples 1 to 4. The results are shown in Table 3.

Evaluation of Skin-Adhesive Property

The skin-adhesive property of the living body-adhesive films of the living body-adhesive sheets of Examples 4 to 9 was evaluated by the following method. Onto skin, 20 μL of a commercially available beauty essence was dropped. Then a 1.5 cm-square living body-adhesive film of each of the living body-adhesive sheets of Examples 4 to 9 was adhered to an anterior forearm region, and the non-woven fabric was released. This process was conducted on sixteen living body-adhesive sheets, and the case where the living body-adhesive film was released from the non-woven fabric and transferred to the skin was deemed a success. The skin adhesion success rate was calculated, and the skin-adhesive property of the living body-adhesive film was evaluated. The results are shown in Table 3.

TABLE 3

| | Weight of non-woven fabric (g/m²) | Evaluation of installation state | Skin adhesion success rate (%) |
|---|---|---|---|
| Example 4 | 20 | A | 100 |
| Example 5 | 30 | AA | 100 |
| Example 6 | 40 | AA | 100 |
| Example 7 | 50 | AA | 100 |
| Example 8 | 60 | AA | 100 |
| Example 9 | 70 | AA | 88 |

Table 3 shows that when the weight of the non-woven fabric is 25 g/m² or more, the adhesion between the living body-adhesive film and the non-woven fabric further increases, and thus the living body-adhesive film can be stably installed onto the non-woven fabric. In contrast, when the weight of the non-woven fabric is 65 g/m² or more, the adhesion between the living body-adhesive film and the non-woven fabric is so high that the living body-adhesive film may not always be smoothly adhered to the skin. Thus, it was found that, as long as weight of the non-woven fabric is 25 to 65 g/m², the living body-adhesive film and the support adhere to each other appropriately, and both stable support of the living body-adhesive film and the increased ease of adhering the living body-adhesive film to skin can be achieved. The weight of the non-woven fabric may be 20 to 70 g/m².

According to the living body-adhesive sheet of the present disclosure, the living body-adhesive film can be adhered to skin without using an adhesive, and the skin feels the adherence of the living body-adhesive film less. Moreover, the living body-adhesive film applies less stress to the skin even when the film stays adhered to the skin for a long time. The living body-adhesive film can be adhered to a living body such as skin, an organ, or the like. The living body-adhesive sheet can be used as, for example, a skin protection sheet or a skin care sheet for the cosmetic or medical purposes. Moreover, the living body-adhesive film can retain active ingredients, such as beauty ingredients, that act on the living body or protect the living body. In addition, the living body-adhesive film may be given a color or a design. The living body-adhesive sheet of the present disclosure can be used as a protective or decorative functional sheet as well as a cosmetic or medical functional sheet.

What is claimed is:

1. A living body-adhesive sheet comprising:
   a living body-adhesive film that has a thickness of 5 μm or less and contains cellulose, wherein a first surface of the living body-adhesive film is configured to adhere to a living body; and
   a support that supports a second surface of the living body-adhesive film, wherein the second surface is opposite to the first surface of the living body-adhesive film,
   wherein the support is formed of a material in which a hydrogen bonding component δH in a Hansen solubility parameter is 2 to 20 MPa$^{1/2}$, and
   wherein the support includes protrusions and recesses, and the living body-adhesive film as a whole covers the protrusions and recesses.

2. The living body-adhesive sheet according to claim 1, wherein the support is a non-woven fabric.

3. The living body-adhesive sheet according to claim 1, wherein the support has a weight of 20 to 70 g/m².

4. The living body-adhesive sheet according to claim 1, wherein the cellulose is regenerated cellulose having a weight-average molecular weight of 30,000 or more.

5. The living body-adhesive sheet according to claim 1, wherein the living body-adhesive film is a self-supporting film having a thickness of 20 to 1300 nm.

6. The living body-adhesive sheet according claim 1, wherein the support is formed of at least one material selected from the group consisting of polyethylene, polyethylene terephthalate, polyacrylonitrile, polystyrene, polyvinyl chloride, polycarbonate, and polyethyleneimide.

7. The living body-adhesive sheet according to claim 6, wherein the support is formed of at least one material selected from the group consisting of polyacrylonitrile and polystyrene.

8. The living body-adhesive sheet according to claim 1, wherein the living body-adhesive film is a single-layer film.

* * * * *